United States Patent
Hwang

(10) Patent No.: US 9,480,465 B2
(45) Date of Patent: Nov. 1, 2016

(54) ORGANISM PARACENTESIS DEVICE AND METHOD THEREOF

(71) Applicant: Richard Hwang, New Taipei (TW)

(72) Inventor: Richard Hwang, New Taipei (TW)

( * ) Notice: Subject to any disclaimer, the term of this patent is extended or adjusted under 35 U.S.C. 154(b) by 131 days.

(21) Appl. No.: 14/147,797

(22) Filed: Jan. 6, 2014

(65) Prior Publication Data
US 2015/0190125 A1 Jul. 9, 2015

(51) Int. Cl.

| | |
|---|---|
| *A61B 5/00* | (2006.01) |
| *B65D 81/00* | (2006.01) |
| *A61B 10/02* | (2006.01) |
| *A61B 10/00* | (2006.01) |
| *A61B 5/15* | (2006.01) |
| *A61M 5/178* | (2006.01) |
| *A61M 5/158* | (2006.01) |
| *A61M 5/19* | (2006.01) |
| *A61M 5/28* | (2006.01) |
| *A61M 5/32* | (2006.01) |
| *A61M 5/24* | (2006.01) |
| *A61M 5/31* | (2006.01) |
| *A61M 5/315* | (2006.01) |

(52) U.S. Cl.
CPC ....... *A61B 10/0283* (2013.01); *A61B 10/0045* (2013.01); *A61B 5/1416* (2013.01); *A61B 5/150251* (2013.01); *A61M 5/1582* (2013.01); *A61M 5/178* (2013.01); *A61M 5/19* (2013.01); *A61M 5/2448* (2013.01); *A61M 5/284* (2013.01); *A61M 2005/1787* (2013.01); *A61M 2005/3123* (2013.01); *A61M 2005/31598* (2013.01); *A61M 2005/3201* (2013.01)

(58) Field of Classification Search
CPC .......... A61B 5/1416; A61B 5/150251; A61B 10/0283; A61B 10/0045; A61M 5/178; A61M 5/19; A61M 5/2448; A61M 5/284; A61M 5/1582; A61M 2005/1787; A61M 2005/3123; A61M 2005/31598; A61M 2005/3201
See application file for complete search history.

(56) References Cited

U.S. PATENT DOCUMENTS

| | | | | |
|---|---|---|---|---|
| 3,604,410 | A * | 9/1971 | Whitacre | A61B 5/1427 600/575 |
| 8,083,722 | B2 * | 12/2011 | McKay | A61B 17/3478 604/173 |
| 2009/0240208 | A1 * | 9/2009 | Cowan | A61M 5/329 604/190 |

\* cited by examiner

*Primary Examiner* — Devin Henson

(57) ABSTRACT

An organism paracentesis device comprises a first tube member and a second tube member. The first tube member comprises an injection tube filled with a medicament, a piston and a first syringe needle. The second tube member comprises a sampling tube and a second syringe needle. Both ends of the second syringe needle are in the form of syringe needle. Using one end of the second syringe needle to penetrate a cover of the sampling tube which is vacuumed, such that the second syringe needle's the other end which is penetrating into an organism will extract a sample from the organism because of the vacuumed sampling tube. The medicament filled in the injection tube is ejected both when the first and second syringe needles are penetrating into and pulled out of the organism, so as to avoid the cells of sampled organism being spread to other places.

4 Claims, 5 Drawing Sheets

ORGANISM PARACENTESIS DEVICE AND METHOD THEREOF

BACKGROUND OF THE INVENTION (1) Field of the Invention

The present invention refers to an organism paracentesis device, especially refers to an organism paracentesis device with two syringe needles, wherein one of the syringe needles is for collecting a sample of organism, while the other one is for injecting, a medicament in order to prevent the cells of sampled organism from being, spread to other places.

(2) Description of the Prior Art

In order to determine whether or not a person has got the cancer, it is necessary to obtain a sample from the organism which is suspected to contain cancer cells. One of the conventional ways to obtain a sample from the organism of the patient is to use a syringe needle to penetrate into the patient's body in order to extract a sample from the organism. Such sampling procedure will require the assistance of ultrasonic scanning in order to make sure the syringe needle has reached the correct position of the suspected organism. If the ultrasonic scanning cannot precisely locate the suspected organism, then Computed Tomography will be employed for assisting the sampling procedure. Currently, using the syringe needle to penetrate into the patient's body and extract a sample from the organism is one of the most efficient ways to sift the Thyroid cancer. The drawback of such sampling procedure is unable to distinguish carcinoma-in-situ and invasive carcinoma, and thus is usually used for sifting suspected patients or monitoring transitional carcinoma cells.

However, the conventional way to process such sampling procedure is to use the syringe needle to directly penetrate into the organism and suck out a sample from the organism by means of a negative pressure inside the syringe needle. There is no protecting means to be applied during the sampling procedure, and thus it is possible that the cells of the sampled organism might stick on outer surface of the syringe needle and leak or spread to nearby areas and even to contaminate nearby tissues when the syringe needle is pulled out from that sampled organism. For example, using the syringe needle to extract a sample from the organism is widely used in diagnosing hepatoma. However, the protruding process of the syringe needle, especially when the syringe needle is pulled out after the sample has been extracted, might also cause the cancer cells to stick on the outer surface of the syringe needle and then spread to other organisms, and thus might increase the risk for the cancer cells to transfer to other organisms.

Accordingly, the present invention provides an organism paracentesis device and method for decreasing the risk of the cells of sampled organism to spread to other organisms.

SUMMARY OF THE INVENTION

A primary objective of the present invention is to provide an organism paracentesis device, which includes two syringe needles; wherein one of the syringe needles is for collecting a sample of organism, while the other one is for injecting a medicament, so as to prevent the cells of sampled organism from being spread to other places.

In order to achieve the objective, the present invention provides an organism paracentesis device, which comprises a first tube member and a second tube member. The first tube member comprises an injection tube, a piston attached with a piston rod and a first syringe needle. The piston is received inside the injection tube. The injection tube is filled with a medicament which can be ejected out from the first syringe needle when the piston rod is pushed. The second tube member comprises a sampling tube and a second syringe needle. Both ends of the second syringe needle are in the form of syringe needle. The second syringe needle has an extracting end located at a bottom end of the second syringe needle and a collecting end located at a top end of the second syringe needle and is able to protrude into the sampling tube. The extracting end of the second syringe needle is capable of penetrating into a sampled organism for extracting a sample from the sampled organism into the sampling tube.

In a preferred embodiment, the lower parts of the first syringe needle and the second syringe needle are abreast with each other; the injection tube of first tube member and an extraction part of the second tube member are integrally formed.

In a preferred embodiment, the second tube member further comprises an extraction part; the collecting end of the second syringe needle is located in the extraction part; the sampling tube is an individual component and yet can be attached to or released from the extraction part; the sampling tube has a cover and an inner compartment; the cover is made of resilient rubber or silica rubber and can seal tightly on a bottom end of the sampling tube; the sampling tube can be inserted and pushed into the extraction part of the second tube member in such a manner that, the collecting end of second syringe needle penetrates through the cover and enters the compartment of sampling tube.

In a preferred embodiment, the medicament is used to kill cancer cells.

In a preferred embodiment, a plurality of side holes are formed on a lower part of a wall of the first syringe needle; these side holes allow the medicament to eject out therefrom.

In a preferred embodiment, the first syringe needle and the second syringe needle are concentric; the second syringe needle is received within the first syringe needle; the first syringe needle and the second syringe needle has the same central axis, so as to form a "needle in needle" structure; a predetermined distance is formed between an inner surface of the first syringe needle and an outer surface of the second syringe needle so as to form a gap between these two needles for allowing the medicament to flow there-through and eject out from the first syringe needle.

In a preferred embodiment, the piston rod is a hollow piston rod having a hollow part which forms an extraction part of the second tube member; the hollow part of the piston rod of the piston is capable of receiving the sampling tube; the second syringe needle is elongated and is extending along the central axis inside the injection tube in such a manner that, the collecting end of the second syringe needle is penetrating through a piston head of the piston, and is extending into the hollow part of the hollow rod of piston.

In order to achieve the objective, the present invention provides an organism paracentesis method, which comprises the steps of:

(A) providing an organism paracentesis device; the organism paracentesis device comprising a first tube member and a second tube member; the first tube member comprising an injection tube, a piston attached with a piston rod and a first syringe needle; the piston being received inside the injection tube; the injection tube being filled with a medicament which can be ejected out from the first syringe needle when the piston rod is pushed; the second tube member comprising a sampling tube and a second syringe needle; both ends of the second syringe needle being in the form of syringe needle; the second syringe needle having an extracting end located at a bottom end of the second syringe needle and a collecting end located at a top end of the second syringe needle; the collecting end being able to protrude into the sampling tube; the extracting end of the second syringe needle being capable of penetrating into a sampled organism for extracting a sample from the sampled organism into the sampling tube;

(B) stabbing the first syringe needle and the second syringe needle into an outer surface of a human skin;

(C) making the first syringe needle and the second syringe needle approaching the sampled organism; when the first syringe needle and the second syringe needle are approaching but not yet reaching an outer surface of the sampled organism, pushing the piston rod of the piston in order to apply the medicament via the first syringe needle to an area nearby the sampled organism;

(D) making at least the extracting end of the second syringe needle penetrating into the sampled organism, and in the mean time, the first syringe needle of the first tube member stopping feeding the medicament;

(E) pushing the sampling tube into an extraction part of the second tube member, and letting the collecting end of the second syringe needle to penetrate through a cover of the sampling tube to contact with an inner compartment of the sampling tube, so as to extract a sample of the sampled organism from the extracting end; and then allowing the sample to enter the inner compartment of the sampling tube via the collecting end of the second syringe needle;

(F) pulling out the sampling tube from the extraction part of the second tube member by having the cover leaving from the collecting end; and (G) pulling out the second syringe needle from the sampled organism; wherein, when the second syringe needle has left an outer surface of the sampled organism but have not yet reached the outer surface of the human skin, pushing the piston rod of the piston to once again inject the medicament; and stop injection of the medicament when the both the first syringe needle and the second syringe needle have been pulled out from the outer surface of the human skin.

BRIEF DESCRIPTION OF THE DRAWINGS

The present invention will now be specified with reference to its preferred embodiment illustrated in the drawings, in which.

DESCRIPTION OF THE PREFERRED EMBODIMENT

Figure 1:
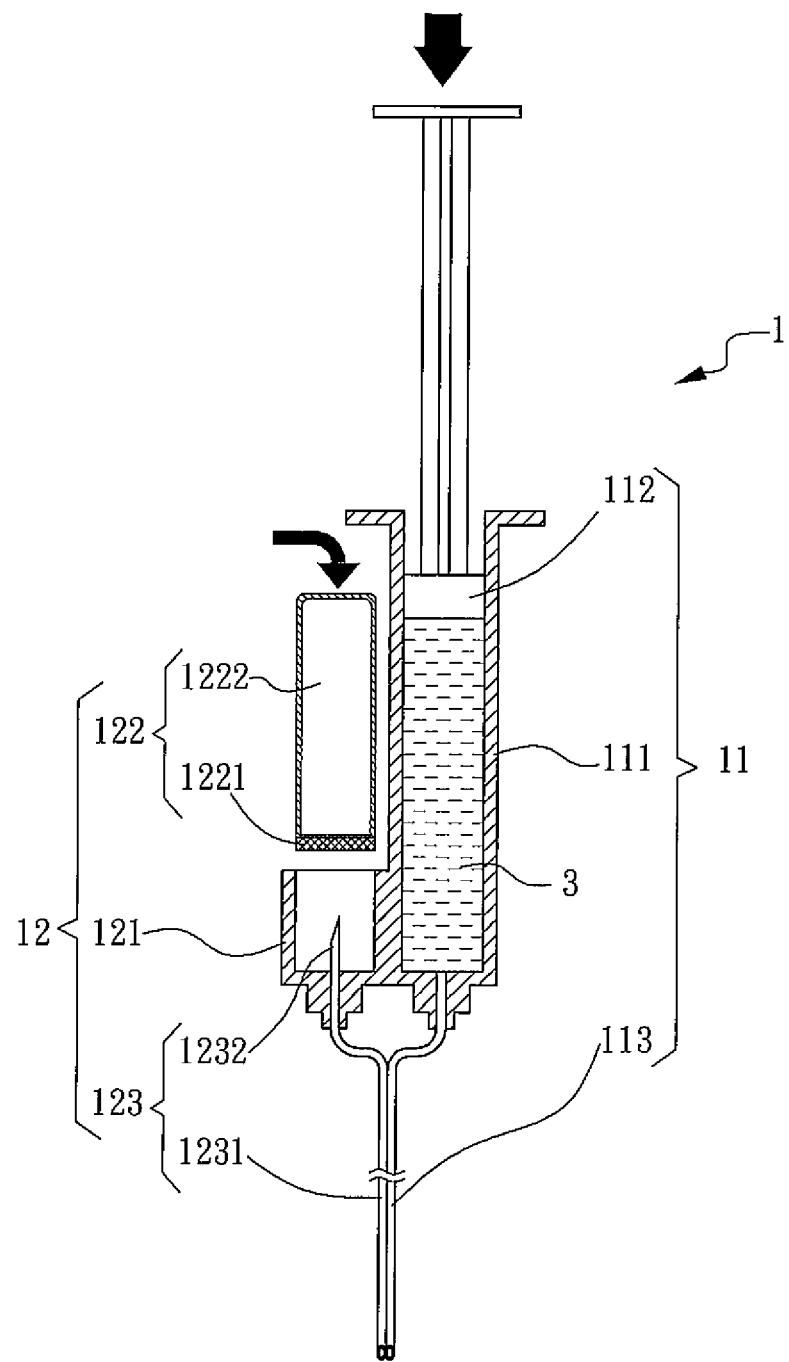
FIG. 1 is a sectional view of a first embodiment of the organism paracentesis device in accordance with the present invention.
Figure 2:
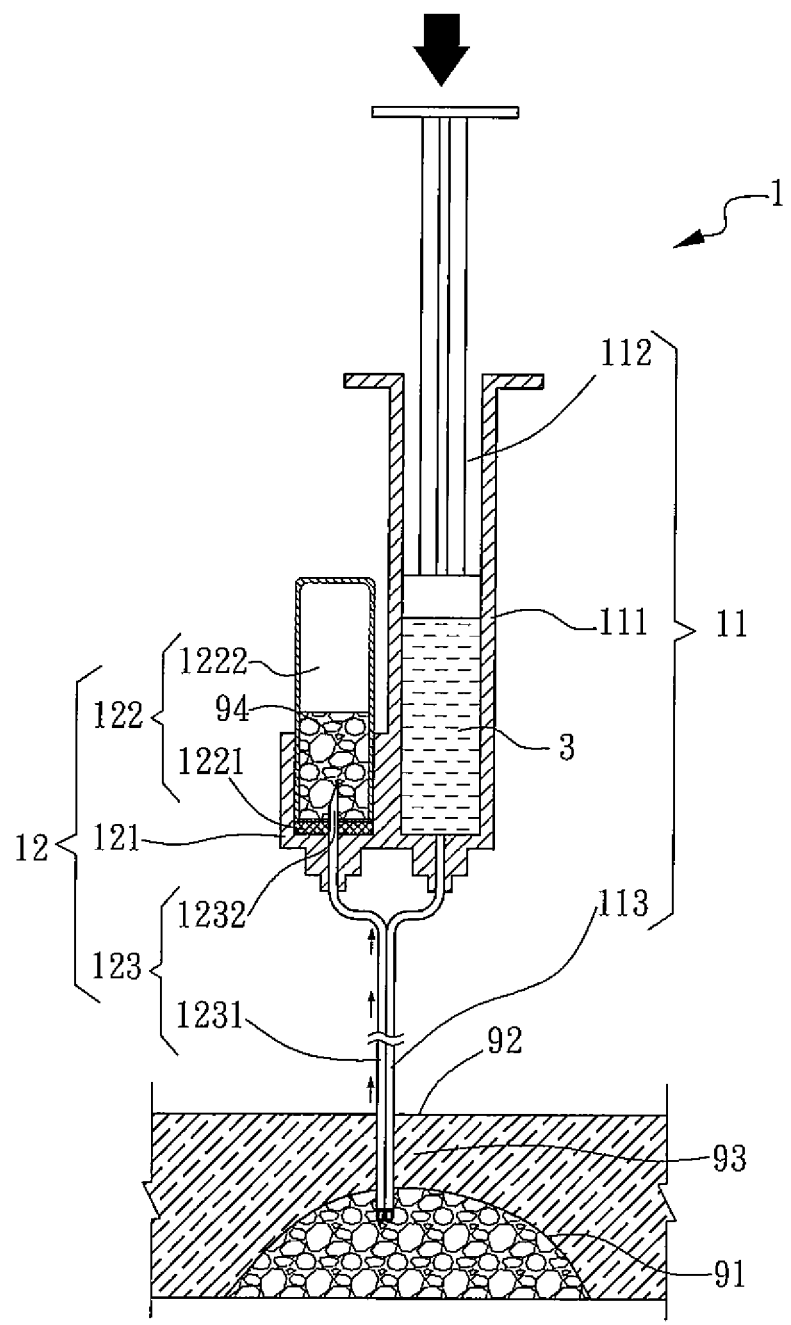
FIG. 2 is a schematic drawing of the organism paracentesis device shown in FIG. 1 in an operational mode.

Please refer to FIG. 1 and FIG. 2, wherein FIG. 1 is a sectional view of a first embodiment of the organism paracentesis device in accordance with the present invention, while FIG. 2 is a schematic drawing of the organism paracentesis device shown in FIG. 1 in an operational mode. In the first embodiment of the present invention, the organism paracentesis device comprises: a first tube member 11 and a second tube member 12. The first tube member 11 further comprises: an injection tube 111, a piston 112 attached with a piston rod and a first syringe needle 113. The second tube member 12 comprises: an extraction part 121, a sampling tube 122 and a second syringe needle 123. The first syringe need 113 is connected to the inner compartment of the injection tube 111. Both ends of the second syringe needle 123 are in the form of syringe needle, which comprises an extracting end 1231 located at the bottom end of the second syringe needle 123 and a collecting end 1232 located at the top end of the second syringe needle 123. The collecting end 1232 is located within the extraction part 121. The extracting end 1231 is for stabbing into and collecting samples from the sampled organism 91. The injection tube 111 is filled with a medicament 3 which is known in the art and is used to kill cancer cells while is relatively harmless to ordinary human organisms and cells. In this first embodiment, the lower parts of the first syringe needle 113 and the second syringe needle 123 are abreast with each other, and the injection tube 111 of first tube member 11 and the extraction part 121 of the second tube member 12 are integrally formed.

The sampling tube 122 of the second tube member 12 is an individual component and yet can be attached to or released from the extraction part 121. The sampling tube 122 includes a cover 1221 and an inner compartment 1222. The cover 1221 is made of resilient rubber or silica rubber and can seal tightly on the bottom end of the sampling tube 122 and thereby keeps the compartment 1222 in a vacuum (or negative pressure) and aseptic condition.

The sampling tube 122 can be inserted and pushed into the extraction part 121 of the second tube member 12 in such a manner that, the collecting end 1232 of second syringe needle 123 penetrates through the cover 1211 and enters the compartment 1222 of sampling tube 122. Because the compartment 1222 is in the vacuum (or negative pressure) condition, the difference of air pressures at two ends 1231, 1232 of the second syringe needle 123 will produce a sucking force at the extracting end 1231, and thus the extracting end 1231 will extract a sample from the sampled organism 91 (such as a tumor or a group of cancer cells) which the extracting end 1231 is contacting with.

Because the lower parts of first syringe needle 131 and second syringe needle 123 are abreast with each other, they will be penetrated into or pulled out from the outer surface 92 of normal tissue 93 and the sampled organism 91 together synchronously. The medicament 3 contained within the injection tube 111 can be ejected out from the first syringe needle 113 at the following timings: (a) when the first and second syringe needles 113, 123 has already penetrated into the outer surface 92 of normal tissue 93 (or human skin) but has not yet reached the area of sampled organism 91, and (h) after the first and second syringe needles 113, 123 has penetrated into the sampled organism 91 and the sample 94 has been obtained by the second syringe needle 123, when the first and second syringe needles 113, 123 has been pulled out from the sampled organism 91 but has not yet reached the outer surface 92 of normal tissue 93 (or human skin). During the above mentioned timings (a) and (b), the medicament 3 contained within the injection tube 111 can be ejected out from the lower end of the first syringe needle 133 constantly, in order to generate an area filled with the medicament 3 between the outer surface of the sampled organism 91 and the outer surface 92 of the normal tissue 93 (or human skin). Therefore, even if the outer surfaces of the first and second syringe needles 113, 123 are stuck with some cancer cells brought from the sampled organism 91, the cancer cells will still be killed by the medicament 3, and thus significantly reduces the risk for the cancer cells to transfer to the normal tissue 93 or other organisms that the first and second syringe needles 113, 123 are passing through.

That means, in the first embodiment of the present invention, the lower part of the first syringe needle 113 of first tube member 11 is extending side by side with the lower part of the second syringe needle 123 of first tube member 12. When proceeding the sampling procedure, the first and second syringe needles 113, 123 are penetrating into the outer surface 92 in the same time. In the mean time, when the bottom ends of the first and second syringe needles 113, 123 have reached the normal tissue 93 but yet have not reached the outer surface of the sampled organism 91, a suitable amount of the medicament 3 contained within the injection tube 111 is ejected out from the bottom end of the first syringe needle 113 by pushing the rod of the piston 112. The ejected medicament 3 will remain in the normal tissue at the area between the outer surface 92 of normal tissue 93 and the outer surface of the sampled organism 91, so as to form a protecting area to prevent the cells of the sampled organism 91 from spreading out to nearby area when the first and second syringe needles 113, 123 are stuck into or pulled out of the sampled organism 91. Because the bottom ends of the first and second syringe needles 113, 123 (including the extracting end 1231) will penetrate into the sampled organism 91, when the first and second syringe needles 113, 123 are pulled out from the sampled organism 91, it is possible that some cells of that sampled organism 91 might attach on the outer surface of the bottom ends of the first and second syringe needles 113, 123 (including the extracting end 1231). The ejected medicament 3 remaining in the previously illustrated protecting area can kill these cells. The medicament 3 is well known in the art for killing cancer cells while is relatively harmless to ordinary human organisms and cells.

When the bottom ends of the first and second syringe needles 113, 123 (including the extracting end 1231) penetrate into the sampled organism 91, the injection tube 111 stops feeding the medicament 3 through the first syringe needle 113. In the mean time, the sampling tube 122 is pushed into the extraction part 121 of the second tube member 12, having the cover 1221 of the sampling tube 122 being penetrated by the collecting end 1232 of the second syringe needle 123. Because the inner compartment 1222 of the sampling tube 122 is in vacuum or negative pressure state, once the collecting end 1232 enters the compartment 1222, the inner hole of the second syringe needle 123 becomes negative pressure as well, and thus the pressure difference will generate a sucking force to suck out a sample 94 from the sampled organism 91. The sample 94 will be sucked out by the extracting end 1231 and then enters the compartment 1222 of the sampling tube 122 via the collecting end 1232. The sampling tube 122 can then be pulled out from the extraction part 121 and sent to the laboratory for analyzing the collected sample 94.

Moreover, when the bottom ends of the first and second syringe needles 113, 123, (including the extracting end 1231) have been pulled out from the sampled organism 91 but yet have not reached the outer surface 92 of normal tissue 93, the medicament 3 contained within the injection tube 111 is once again ejected out from the lower end of the first syringe needle 133 constantly by pushing the rod of the piston 112, until both the first and second syringe needles 113, 123 (including the extracting end 1231) leave the outer surface 92 of the normal tissue 93 completely, so as to increase the protecting effect of the aforementioned protecting area.

Figure 3:
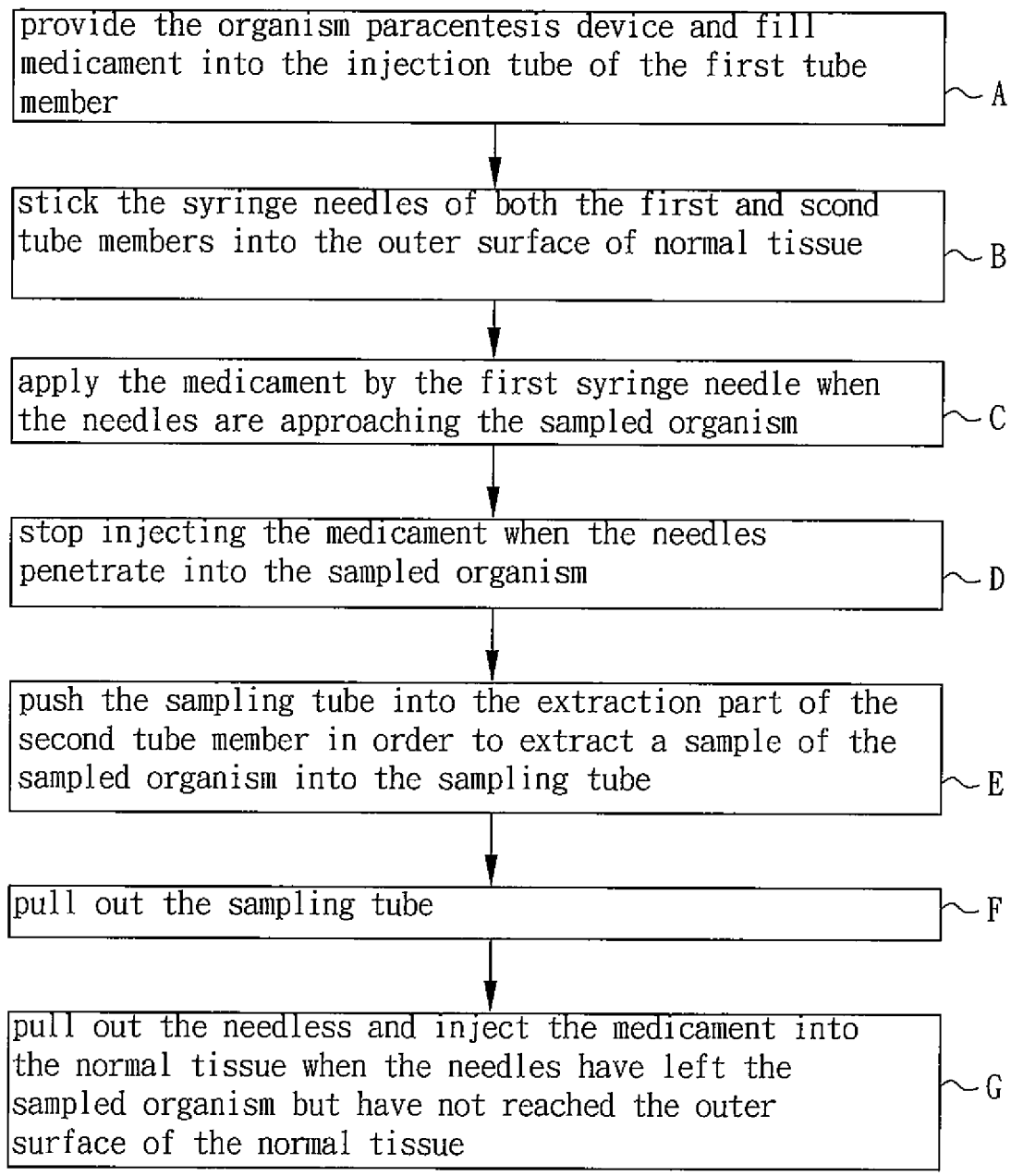
FIG. 3 is a flow chart illustrating the first embodiment of the organism paracentesis method in accordance with the present invention.

Please refer to FIG. 3, which is a flow chart illustrating the first embodiment of the organism paracentesis method in accordance with the present invention. The organism paracentesis method uses the previously illustrated organism paracentesis device 1 of the present invention to perform the sampling procedure, which comprises the following steps:

(A) providing an organism paracentesis device 1 as previously illustrated in FIG. 1 and FIG. 2, and filling the medicament 3 into the injection tube 111 of the first tube member 11;

(B) stabbing the first syringe needle 113 of the first tube member 11 and the second syringe needle 123 of the second tube member 12 into the outer surface 92 of the normal tissue 93 in the same time;

(C) when the first and second syringe needles 113, 123 are approaching but not yet reaching the outer surface of the sampled organism 91, pushing a rod of the piston 112 of the first tube member 11 in order to apply the medicament 3 via the first syringe needle 113 to the normal tissue 93 at an area nearby the sampled organism 91;

(D) when the first and second syringe needles 113, 123 are penetrating into the sampled organism 91, the first syringe needle 113 of the first tube member 11 stops feeding the medicament 3;

(E) pushing the sampling tube 122 into the extraction part 121 of the second tube member 12, and letting the collecting end 1232 of the second syringe needle 123 to penetrate through the cover 1221 of the sampling tube 122 to contact with the antiseptic and vacuumed inner compartment 1222 of the sampling tube 122, so as to generate a sucking force at the extracting end 1231 of the second syringe needle 123 by means of pressure difference for extracting a sample 94 of the sampled organism 91 from the extracting end 1231; and then allowing the sample 94 to enter the compartment 122 of the sampling tube 122 via the collecting end 1232 of the second syringe needle 123;

(F) pulling out the sampling tube 122 from the extraction part 121 of the second tube member 12 by having the cover 1221 leaving from the collecting end 1232; and (G) pulling out the first and second syringe needles 113, 123 from the sampled organism 91; wherein, when the first and second syringe needles 113, 123 have left the surface of the sampled organism 91 but have not yet reached the outer surface 92 of the normal tissue 93, pushing the rod of the piston 112 to once again inject the medicament 3 to the normal tissue 93 at the area nearby the sampled organism 91; and stop injection of the medicament 3 when the first and second syringe needles 113, 123 have been pulled out from the outer surface 92 of the normal tissue 93.

In another embodiment of the organism paracentesis method of the present invention, the above mentioned steps (F) and (G) can swap, which means, the needles 113, 123 can be pulled out first, and then release the sampling tube from the extraction part of the second tube member.

Since the following embodiments described below have similar components and features like the one illustrated above, thus same components and structures will be assigned with the same numerals and names, while similar components and structures will be assigned with the same names but will add an additional alphabet after their numerals, and no detail descriptions will be provided for these same or similar components and structures.

Figure 4:
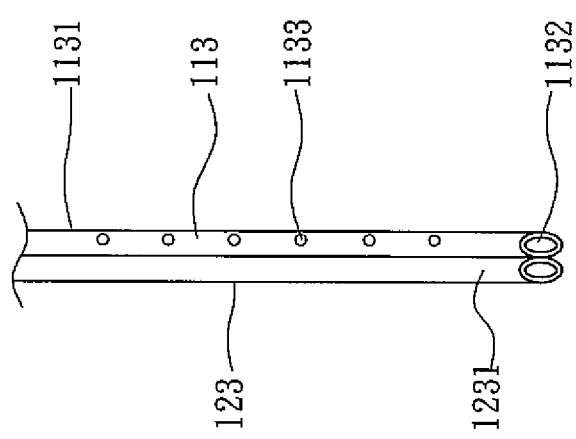
FIG. 4 is a partially enlarged view of a second embodiment of the organism paracentesis device in accordance with the present invention.

Please refer to FIG. 4, which is a partially enlarged view of a second embodiment of the organism paracentesis device in accordance with the present invention. The organism paracentesis device of the second embodiment shown in FIG. 4 have almost all the same components as which previously described in the first embodiment shown in FIG. 1 and FIG. 2. The only difference between the organism paracentesis device shown in FIG. 4 and the one shown in FIG. 1 is that, in this second embodiment shown in FIG. 4, there are a plurality of side holes 1133 being formed on the wall of the first syringe needle 113. These side holes 1133 are through holes connecting the outer surface 1131 of the first syringe needle 113 and the inner surface 1132 of the first syringe needle 113. These side holes 1133 allow the medicament 3 to eject out from them, so as to increase the size of the protecting area, and thus decrease the risk for the cancer cells to transfer to other organisms.

Figure 5:
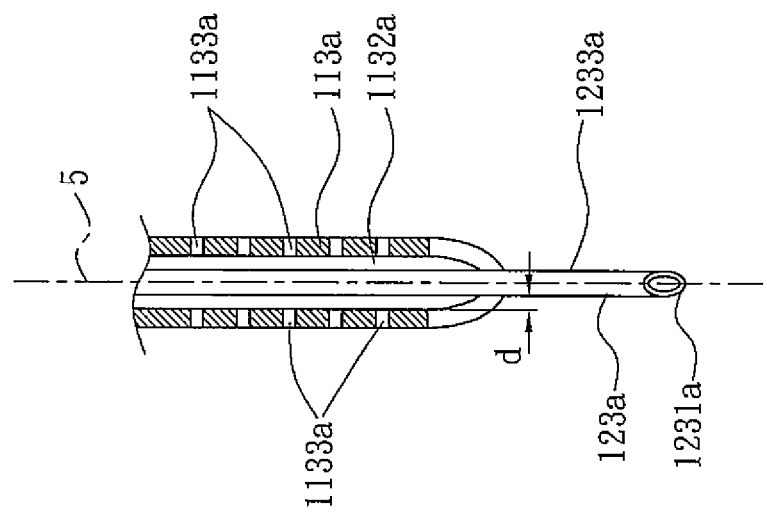
FIG. 5 is a partially enlarged sectional view of a third embodiment of the organism paracentesis device in accordance with the present invention.
Figure 6:
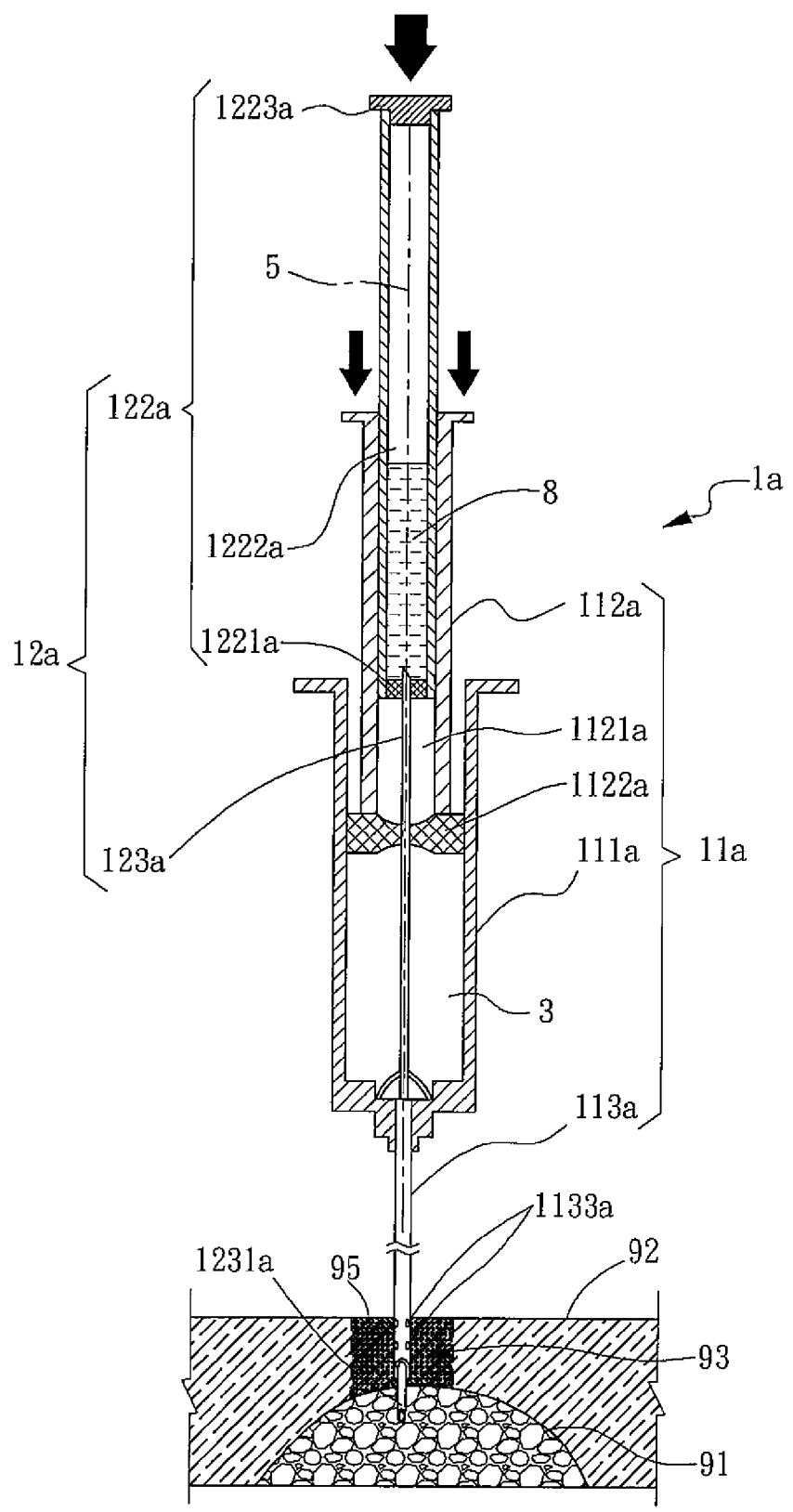
FIG. 6 is the sectional view of the third embodiment of the organism paracentesis device in accordance with the present invention.

Please refer to FIG. 5 and FIG. 6, wherein, FIG. 5 is a partially enlarged sectional view of a third embodiment of the organism paracentesis device in accordance with the present invention, while FIG. 6 is the sectional view of the third embodiment of the organism paracentesis device in accordance with the present invention.

The difference between the third embodiment shown in FIG. 5 and FIG. 6 and the second embodiment shown in FIG. 4 includes the following points. Firstly, the organism paracentesis device 1a of the third embodiment shown in FIG. 5 and FIG. 6 comprises a concentric syringe needle structure. That means, the first syringe needle 113a and the second syringe needle 123a are concentric; wherein the second syringe needle 123a is received within the inner compartment of the first syringe needle 113a, and the central axis of both the first and second syringe needles 113a, 123a is the same central axis 5. The second syringe needle 123a is located within the first syringe needle 113a to form a "needle in needle" structure. In addition, there is a predetermined distance "d" between the inner surface 1132a of the first syringe needle 113a and the outer surface 1233a of the second syringe needle 123a, so as to form a gap (passage) between these two needles 113a, 123a for allowing the medicament 3 to flow there-through and eject out from the first syringe needle 113a. In addition, when using the organism paracentesis device 1a to collect the sample, the extracting end 1231a of the second syringe needle 123a can protrude out of the bottom tip of the first syringe needle 113a in order to penetrate into the sampled organism 91 for extracting the sample 94.

As shown in FIG. 6, in the third embodiment of the organism paracentesis device 1a of the present invention, the piston 112a of the first tube member 11a has a hollow rod which substantially becomes the extraction part of the second tube member 12a. Which means, the second tube member 12a is formed on the hollow rod of the piston 112a and is located within the injection tube 111a of the first tube member 11a and can slide along the central axis 5 together with the piston 112a. The hollow part 1121a of the hollow rod of piston 112a becomes the extraction part of the second tube member 12a and is capable of receiving the sampling tube 122a, wherein the sampling tube 122a is an individual component which can be pushed into or pulled out from the hollow part 1121a of the hollow rod of piston 112a. The second syringe needle 123a is elongated and is extending along the central axis 5 inside the injection tube 222a in such a manner that, the collecting end of the second syringe needle 123a is penetrating through the piston head 1122a of the piston 112a, and is extending into the hollow part 1121a of the hollow rod of piston 112a. The sampling tube 122a has a cover 1221a, a plug 1223a and an inner compartment 1222a for receiving the sample of the sampled organism 91 extracted by the extracting end 1231a of the second syringe needle 123a. The cover 1221a is made of resilient rubber or silica rubber and can seal tightly on the bottom end of the sampling tube 122a and thereby keeps the compartment 1222a in a vacuum (or negative pressure) and aseptic condition. In addition, a cultivation solution 8 can be filled within the compartment 1222a of the sampling tube 122a in advance before starting the sampling procedures. The cultivation solution 8 is well known in the art for helping the conservation of the sample of sampled organism 91. When plugging the sampling tube 122a into the hollow part 1121a of the hollow rod of piston 112a, the cover 1221a of the sampling tube 122a will be penetrated by the collecting end (top end) of the second syringe needle 123a. Because the compartment 1222a is in the negative pressure condition (although filled with some cultivation solution 8), the difference of air pressures at two ends of the second syringe needle 123a will produce a sucking force at the extracting end 1231a, and thus the extracting end 1231a will extract a sample from the sampled organism 91 (such as a tumor or a group of cancer cells) which the extracting end 1231a is contacting with. There is a small gap between the outer surface of the sampling tube 122a and the inner surface of the hollow rod of the piston 112a in order to allow the air to pass through when the sampling tube 122a is pushed into or pulled out of the hollow part 1121a of the hollow rod of the piston 112a.

When performing the sampling procedure, firstly the bottom tip of the first syringe needle 113a of the first tube member 11a stabs into the outer surface 92 of normal tissues 93 (or human skin). When the first syringe needle 113a is approaching but yet has not reached the sampled organism 91, the medicament 3 contained in the injection tube 111a is ejected out from the first syringe needle 113a by pushing the top end of the piston rod of the piston 112a, so as to form a protecting area 95 which is soaked by the medicament 3. The protecting area 95 is in the normal tissue 93 and is extending along the passage of needles 113a. 123a between the outer surface 92 of normal tissue 93 and the outer surface of the sampled organism 91. When the extracting end 1231a of the second syringe needle 123a penetrates into the sampled organism 91, stop pushing the top end of the hollow piston rod of the piston 112a in order to stop ejecting the medicament 3 from the first syringe needle 113a. Then, plugging and pushing the sampling tube 122a into the hollow part 1121a of the piston rod of the piston 112a until the cover 1221a of the sampling tube 122a is penetrated by the collecting end (top end) of the second syringe needle 123a. Therefore, the pressure difference caused by the negative pressure inside the sampling tube 122a will generate a sucking force at the extracting end 1231a of the second syringe needle 123a. Thus, the sample of the sampled organism 91 will be extracted by the extracting end 1231a of the second syringe needle 123a and sucked into the compartment 1222a of the sampling tube 122a, and soaked within the cultivation solution 8. The sampling tube 122a is then pulled out from the hollow part 1121a of the piston rod of the piston 112a and is sent to the laboratory for analysis. And then, the extracting end 1231a of the second syringe needles 123a is pulled out of the sampled organism 91. Once the extracting end 1231a of the second syringe needles 123a leaves the outer surface of the sampled organism 91, the medicament 3 can once again applied to the protecting area 95 by pushing the top end of the piston rod of the piston 112a, until both the first and second syringe needles 113a, 123a leave the outer surface 92 of the normal tissue 93.

In this embodiment, the second syringe needle 123a is fixed to the inner wall of the injection tube 111a and cannot move together with the piston 112a. Which means, when the piston 112a is pushed to cause the piston head 1122a moving downward within the injection tube 111a, the piston head 1122a will also slide along the second syringe needle 123a, because the second syringe needle 123a will not move with the piston head 1122a. However, in yet another embodiment of the present invention, the second syringe needle 123a can also be fixed to the piston head 1122a and thus is movable with the piston head 1122a along the central axis 5 when the top end of the hollow piston rod of the piston 112a is pushed downward. That means, when the top end of the hollow piston rod of the piston 112a is pushed downward, not only the medicament 3 contained within the injection tube 111a will be ejected out from the first syringe needle 113a, but also the extracting end 1231a of the second syringe needle 123a will protrude out from the bottom tip of the first syringe needle 113a.

The organism paracentesis method uses the previously illustrated third embodiment of the organism paracentesis device 1a of the present invention to perform the sampling procedure, which comprises the following steps:

(1) providing the organism paracentesis device 1a as shown in FIG. 5 and FIG. 6, filling a predetermined amount of medicament 3 into the injection tube 111a, and filling another predetermined amount of cultivation solution 8 into the sampling tube 122a while keeping the inner compartment 1222a of the sampling tube 122a in a negative pressure condition;

(2) stabbing the first syringe needle 113a of the first tube member 11a and the second syringe needle 123a of the second tube member 12a into the outer surface 92 of the normal tissue 93;

(3) when the first syringe needles 113a is approaching but not yet reaching the outer surface of the sampled organism 91, pushing the top of the piston rod of the piston 112a in order to apply the medicament 3 via the first syringe needle 113a to the normal tissue 93 at an area nearby the sampled organism 91, so as to form a protecting area 95 soaked with medicament in the normal tissue 93;

(4) when the extracting end 1231a of the second syringe needle 123a penetrates into the sampled organism 91, push the sampling tube 122a into the hollow part 1121a of the rod of the piston 112a, and letting the collecting end (top end) of the second syringe needle 123a to penetrate through the cover 1221a of the sampling tube 122a to contact with the inner compartment 1222a of the sampling tube 122a, so as to generate a sucking force at the extracting end 1231a of the second syringe needle 123a for extracting a sample 94 of the sampled organism 91 from the extracting end 1231; and then allowing the sample 94 to enter the compartment 122a of the sampling tube 122a and soak in the cultivation solution 8;

(5) pulling out the sampling tube 122a from the hollow part 1121a of the rod of the piston 112a by having the cover 1221a leaving from the collecting end (top end) of the second syringe needle 123a; and (6) pulling out the second syringe needle 123a from the sampled organism 91; wherein, when the second syringe needle 123a has left the surface of the sampled organism 91 but has not yet reached the outer surface 92 of the normal tissue 93, pushing the hollow rod of the piston 112a to once again inject the medicament 3 to the normal tissue 93 at the area nearby the sampled organism 91; and stop injection of the medicament 3 when the first and second syringe needles 113a, 123a have been pulled out from the outer surface 92 of the normal tissue 93.

While the present invention has been particularly shown and described with reference to a preferred embodiment, it will be understood by those skilled in the art that various changes in form and detail may be without departing from the spirit and scope of the present invention.

I claim:

1. An organism paracentesis device, comprising:
a first tube member comprising an injection tube, a piston attached with a piston rod and a first syringe needle; the piston being received inside the injection tube; the injection tube being filled with a medicament which is ejected out from the first syringe needle when the piston rod is pushed; and
a second tube member comprising a sampling tube and a second syringe needle; both ends of the second syringe needle being in the form of syringe needle; the second syringe needle having an extracting end located at a bottom end of the second syringe needle and a collecting end located at a top end of the second syringe needle and being able to protrude into the sampling tube; the extracting end of the second syringe needle being capable of penetrating into a sampled organism for extracting a sample from the sampled organism into the sampling tube;
wherein the second tube member further comprises an extraction part; the collecting end of the second syringe needle is located in the extraction part; the sampling tube is an individual component and yet is able to be attached to the extraction part in a releasable manner; the sampling tube has a cover and an inner compartment; the cover is made of resilient rubber or silica rubber and seals on a bottom end of the sampling tube; the sampling tube is able to be inserted and pushed into the extraction part of the second tube member in such a manner that, the collecting end of second syringe needle penetrates through the cover and enters the compartment of sampling tube;
wherein the medicament is used to kill cancer cells;
wherein a plurality of side holes are formed on a lower part of a wall of the first syringe needle; these side holes allow the medicament to eject out there-from, so as to increase a size of a protecting area where the medicament is ejected for killing the cancer cells.

2. The organism paracentesis device of claim 1, wherein lower parts of the first syringe needle and the second syringe needle are abreast with each other; the injection tube of first tube member and an extraction part of the second tube member are integrally formed.

3. An organism paracentesis method, comprising steps of:
(A) providing an organism paracentesis device; the organism paracentesis device comprising a first tube member and a second tube member; the first tube member comprising an injection tube, a piston attached with a piston rod and a first syringe needle; the piston being received inside the injection tube; the injection tube being filled with a medicament which is ejected out from the first syringe needle when the piston rod is pushed; the second tube member comprising a sampling tube and a second syringe needle; both ends of the second syringe needle being in the form of syringe needle; the second syringe needle having an extracting end located at a bottom end of the second syringe needle and a collecting end located at a top end of the second syringe needle; the collecting end being able to protrude into the sampling tube; the extracting end of the second syringe needle being capable of penetrating into a sampled organism for extracting a sample from the sampled organism into the sampling tube;

wherein the second tube member further comprises an extraction part; the collecting end of the second syringe needle is located in the extraction part; the sampling tube is an individual component and yet is able to be attached to the extraction part in a releasable manner; the sampling tube has a cover and an inner compartment; the cover is made of resilient rubber or silica rubber and seals on a bottom end of the sampling tube; the sampling tube is able to be inserted and pushed into the extraction part of the second tube member in such a manner that, the collecting end of second syringe needle penetrates through the cover and enters the compartment of sampling tube;

wherein the medicament is used to kill cancer cells;

wherein a plurality of side holes are formed on a lower part of a wall of the first syringe needle; these side holes allow the medicament to eject out there-from, so as to increase a size of a protecting area where the medicament is ejected for killing the cancer cells;

(B) stabbing the first syringe needle and the second syringe needle into an outer surface of a human skin;

(C) making the first syringe needle and the second syringe needle approaching the sampled organism; when the first syringe needle and the second syringe needle are approaching but not yet reaching an outer surface of the sampled organism, pushing the piston rod of the piston in order to apply the medicament via the side holes of the first syringe needle to an area nearby the sampled organism;

(D) making at least the extracting end of the second syringe needle penetrating into the sampled organism, and meanwhile, the first syringe needle of the first tube member stopping feeding the medicament;

(E) pushing the sampling tube into the extraction part of the second tube member, and letting the collecting end of the second syringe needle to penetrate through the cover of the sampling tube to contact with the inner compartment of the sampling tube, so as to extract the sample of the sampled organism from the extracting end; and then allowing the sample to enter the inner compartment of the sampling tube via the collecting end of the second syringe needle;

(F) pulling out the sampling tube from the extraction part of the second tube member by having the cover leaving from the collecting end; and (G) pulling out the second syringe needle from the sampled organism; wherein, when the second syringe needle has left an outer surface of the sampled organism but have not yet reached the outer surface of the human skin, pushing the piston rod of the piston to once again inject the medicament; and stop injection of the medicament when the both the first syringe needle and the second syringe needle have been pulled out from the outer surface of the human skin.

4. The organism paracentesis method of claim 3, wherein lower parts of the first syringe needle and the second syringe needle are abreast with each other; the injection tube of first tube member and an extraction part of the second tube member are integrally formed.

\* \* \* \* \*